US008435560B2

(12) United States Patent
Marteaux et al.

(10) Patent No.: US 8,435,560 B2
(45) Date of Patent: May 7, 2013

(54) POLYNUCLEAR MICROCAPSULES

(75) Inventors: Leon Andre Marteaux, Auderghem (BE); Brett Lee Zimmerman, Frankenmuth, MI (US)

(73) Assignee: Dow Corning Corporation, Midland, MI (US)

( * ) Notice: Subject to any disclaimer, the term of this patent is extended or adjusted under 35 U.S.C. 154(b) by 525 days.

(21) Appl. No.: 12/519,403

(22) PCT Filed: Dec. 21, 2007

(86) PCT No.: PCT/US2007/088623
§ 371 (c)(1),
(2), (4) Date: Mar. 9, 2010

(87) PCT Pub. No.: WO2008/083092
PCT Pub. Date: Jul. 10, 2008

(65) Prior Publication Data
US 2010/0172999 A1     Jul. 8, 2010

Related U.S. Application Data

(60) Provisional application No. 60/877,583, filed on Dec. 28, 2006.

(51) Int. Cl.
*A61K 9/66* (2006.01)
(52) U.S. Cl.
USPC .................................................. 424/455
(58) Field of Classification Search .................. None
See application file for complete search history.

(56) References Cited

U.S. PATENT DOCUMENTS

| 4,122,029 | A | 10/1978 | Gee et al. |
| 4,169,069 | A | 9/1979 | Unger et al. |
| 4,853,474 | A | 8/1989 | Bahr et al. |
| 5,035,832 | A | 7/1991 | Takamura et al. |
| 5,811,487 | A | 9/1998 | Schulz, Jr. et al. |
| 6,238,650 | B1 | 5/2001 | Lapidot et al. |
| 6,303,149 | B1 | 10/2001 | Magdassi et al. |
| 2004/0256748 | A1* | 12/2004 | Seok et al. ............... 264/4.1 |

FOREIGN PATENT DOCUMENTS

| DE | 19954772 | 5/2001 |
| EP | 0120967 | 6/1987 |
| EP | 281034 | 9/1988 |
| EP | 0174377 | 11/1988 |
| EP | 1145708 | 10/2001 |
| EP | 934773 | 2/2004 |
| FR | 2876028 | 4/2006 |
| GB | 2416524 | 2/2006 |
| JP | 64-30633 | 5/1994 |
| JP | 09118726 | 5/1997 |

(Continued)

OTHER PUBLICATIONS

Siltech Publication, Silicone POlyether Surfactants and Derivatives Technical Data, Jun. 1, 2004.*

(Continued)

*Primary Examiner* — Paul Dickinson
(74) *Attorney, Agent, or Firm* — Alan Zombeck

(57) ABSTRACT

A process is disclosed for preparing polynuclear microcapsules by polymerizing an alkoxysilane at the oil/water interface of a multiple phase emulsion to form a suspension of polynuclear microcapsules. Also disclosed are polynuclear micro-capsules optionally comprising a hydrophilic active and uses thereof.

10 Claims, 2 Drawing Sheets

FOREIGN PATENT DOCUMENTS

| | | |
|---|---|---|
| JP | 09-290146 | 11/1997 |
| JP | 2001-038193 | 2/2001 |
| JP | 2003238342 | 8/2003 |
| JP | 2004331617 | 11/2004 |
| WO | WO 98/31333 | 7/1998 |
| WO | WO 00/09652 | 2/2000 |
| WO | WO 00/71084 | 11/2000 |
| WO | WO0124762 | 4/2001 |
| WO | WO 01/80823 | 11/2001 |
| WO | WO0220148 | 3/2002 |
| WO | WO03011239 | 2/2003 |
| WO | WO03041666 | 5/2003 |
| WO | WO 03/066209 | 8/2003 |
| WO | WO 2005/009604 | 2/2005 |
| WO | WO 2005/053631 | 6/2005 |
| WO | WO 2006/061124 | 6/2006 |
| WO | WO2006/084339 | 8/2006 |
| WO | WO 2006/133519 | 12/2006 |
| WO | WO 2007/000316 | 1/2007 |
| WO | WO2008002637 | 1/2008 |

OTHER PUBLICATIONS

Lee M H et al: Preparation of silica particles encapsulating retinol using o/w/o multiple emulsions, Journal of Colloid and Interface Science, Aug. 1, 2001, pp. 83-89.

Fujiwara Masahiro et al: Direct encapsulation of BSA and DNA into silica microcapsules (hollow spheres), Journal of Biomedical Materials Research, Part A, Apr. 2007, vol. 81, No. 1, pp. 103-112.

* cited by examiner

POLYNUCLEAR MICROCAPSULES

CROSS REFERENCE TO RELATED APPLICATIONS

This application is a U.S. national stage filing under 35 U.S.C. §371 of PCT Application No. PCT/US07/88623 filed on Dec. 21, 2007, currently pending, which claims the benefit of U.S. Provisional Patent Application No. 60/877,538 filed Dec. 28, 2006 under 35U.S.C. §119 (e). PCT Application No. PCT/US07/88623 and U.S. Provisional Patent Application No. 60/877,538 are hereby incorporated by reference.

TECHNICAL FIELD

This invention relates to polynuclear microcapsules and to a process for preparing polynuclear microcapsules by polymerizing an alkoxysilane at the oil/water interface of a multiple phase emulsion to form a suspension of polynuclear microcapsules.

BACKGROUND

Only few encapsulation techniques have been described in the art as a manner for protecting and delivering cosmetic/pharmaceutical actives or for protecting the bioactivity of biologics, i.e. stabilization such as enzymes and cells.

One technique in the art is to entrap hydrophilic cosmetic, chemical, biological or pharmaceutical active material compositions in liposomes or vesicular structures. Their structure integrities are known to be sensitive to the presence of surfactants. Another entrapment technique is to encapsulate hydrophilic cosmetic, chemical, biological or pharmaceutical active material compositions in water in oil in water (W/O/W) multiple emulsions. For example, EP 0120967 B1 describes a process of making W/O/W oil and fat composition for food. The oil phase is not an alkoxysilane composition. EP 0174377 B2 describes a method of making W/O/W complex emulsion for medicinal and cosmetic use.

WO-A-98/31333 describes sunscreen-doped sol-gel materials and a method for their preparation comprising condensation polymerization of a metal or semi-metal alkoxide or ester in the presence of at least one sunscreen ingredient, resulting in the entrapment of the sunscreen ingredients within the formed sol-gel matrix.

U.S. Pat. No. 6,303,149 describes a process for preparing sol-gel microcapsules loaded with functional molecules by emulsifying sol-gel precursors and the functional molecules in an aqueous solution, and mixing the emulsion with an acidic, neutral or basic aqueous solution to obtain a suspension of microcapsules.

EP-A-281034 describes a perfume encapsulated and/or clathrated in a matrix of an organic polymer prepared from a metal alkoxide such as tetraethyl orthosilicate (TEOS). An aqueous dispersion or solution of perfume and TEOS is treated with an acid catalyst to cause hydrolysis, then with a base catalyst to cause polymerization to a gel.

EP-A-934773 describes microcapsules whose capsule wall comprises organopolysiloxane synthesized by condensing a compound of the formula $R_nSi(OH)_mY_{(4-m-n)}$ where m=1-4; n=0-3; R represents an organic group with a C atom directly bonded to a Si atom; and Y is an alkoxy group, H or a siloxy group.

WO-A-01/80823 describes a therapeutic or cosmetic composition comprising microcapsules of diameter 0.1-100 μM having a core-shell structure. The core includes at least one active. The shell comprises an inorganic polymer obtained by a sol-gel process, and releases the active after topical application.

WO-A-03/066209 describes a process of making lipophilic cosmetic, chemical, or pharmaceutical active material compositions encapsulated within a shell obtained from the emulsion polymerization products of tetraalkoxysilane. The process of making these microcapsules is a one kettle process without removal of the continuous phase.

WO-A-03/066209 describes an encapsulation process by ex-situ emulsion polymerization from tetraalkoxysilanes and the surfactant concentration in the starting cationic emulsion.

FR 2876028A1 describes the encapsulation of plant extracts in precipitated silica. This process is not suitable for the encapsulation of hydrophilic cosmetic, chemical, biological or pharmaceutical active material compositions.

JP 2004331617 A2 and JP 2003238342 A2 describe W/O emulsion compositions containing silylated peptide-silane compound copolymers for cosmetics.

The bioactivity of biologics is very sensitive to the conditions in which they are used. Many attempts to improve their robustness have been made. One consists of immobilization of the biologics by covalent bonding onto surfaces. However the immobilization can lead to significant biologic loss and only delays the loss of bioactivity.

A recent approach consists of the encapsulation of biologics into a sol-gel matrix coated onto a surface. Some drawbacks to the use of this approach is that the shrinking of the matrix during the sol-gel process can affect the enzymatic molecular conformation and therefore its activity. In addition, a coating limits the surface for exchange between the encapsulated biologic and the substrate present in the reaction vessel.

Many of these aforementioned processes are not suitable for the encapsulation of hydrophilic materials because of the conditions or techniques used. In addition, the capsules formed by the aforementioned processes do not provide capsules suitable for long-term entrapment of hydrophobic materials or improving the stability of hydrophilic materials such as biologics. Thus, there is a need for a process for encapsulating hydrophilic materials such as cosmetics, chemicals, biologics or pharmaceutical active material compositions wherein the encapsulated materials have improved stability or the ability to entrap the hydrophobic material.

SUMMARY OF THE INVENTION

The present inventors have discovered an improved encapsulation process to produce stable compositions by polymerizing an alkoxysilane at the oil/water interface of a multiple phase emulsion of hydrophilic actives to form polynuclear microcapsules that are useful to encapsulate hydrophilic materials such as cosmetic, chemical, biological or pharmaceutical active materials which result in compositions having improved stability.

The invention relates to a polynuclear microcapsule which comprises an outer-capsule wherein the outer-capsule comprises an outer-shell and a plurality of inner-capsules, wherein each of the inner-capsules comprises an inner-shell and an aqueous phase core, wherein the outer-shell and the inner-shell further comprise a silica or an organofunctional silica.

The invention relates to a polynuclear microcapsule which comprises an outer-capsule, wherein the outer-capsule comprises an outer-shell and a plurality of inner-capsules, wherein each of the inner-capsules comprises an inner-shell and an aqueous phase core, wherein the outer-shell and the inner-shell further comprise a silica or an organofunctional silica, and the silica or organofunctional silica comprises a reaction product from the polymerization of an alkoxysilane or a mixture of alkoxysilanes at the oil/water interfaces of a multiple phase emulsion.

The invention relates to a polynuclear microcapsule which comprises an outer-capsule, wherein the outer-capsule comprises an outer-shell and a plurality of inner-capsules, wherein each of the inner-capsules comprises an inner-shell and an aqueous phase core comprising a hydrophilic active, wherein the outer-shell and the inner-shell further comprise a silica or an organofunctional silica.

The invention relates to a polynuclear microcapsule which comprises an outer-capsule, wherein the outer-capsule comprises an outer-shell and a plurality of inner-capsules, wherein each of the inner-capsules comprises an inner-shell and an aqueous phase core comprising a hydrophilic active, wherein the outer-shell and the inner-shell further comprise a silica or an organofunctional silica and the silica or organofunctional silica comprises a reaction product from the polymerization of an alkoxysilane or a mixture of alkoxysilanes at the oil/water interfaces of a multiple phase emulsion.

The invention also relates to compositions comprising a polynuclear microcapsule of the invention in association with at least one pharmaceutically-acceptable carrier, adjuvant or diluent.

The invention also relates to the use of the polynuclear microcapsules of the invention to stabilize a hydrophilic active.

This invention also relates to a process for preparing polynuclear microcapsules comprising:

I) mixing
  A) a first emulsifier,
  B) an alkoxysilane,
  C) optionally a hydrophilic active,
with sufficient water or water soluble solvent to form an emulsion having the alkoxysilane in the continuous phase;

II) admixing to the emulsion having the alkoxysilane in the continuous phase
  D) a second emulsifier to form a multiple phase emulsion;

III) polymerizing the alkoxysilane at the oil/water interface of the multiple phase emulsion to form a suspension of polynuclear microcapsules.

This invention also relates to the microcapsules, and suspensions of the microcapsules, prepared according to present process.

DETAILED DESCRIPTION OF THE INVENTION

Figure 1:
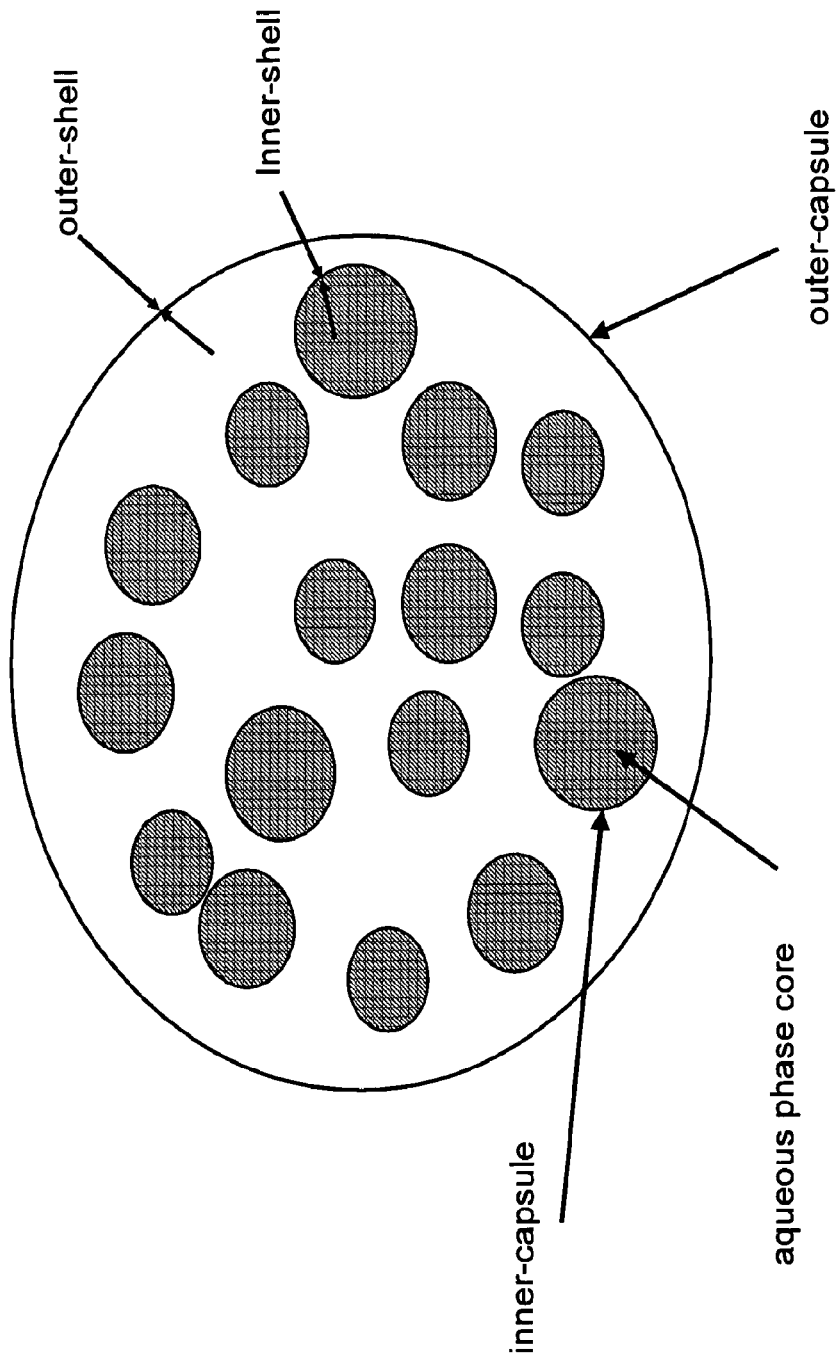
FIG. 1 is a graphic illustration of a representative polynuclear microcapsule of the invention.
Figure 2:
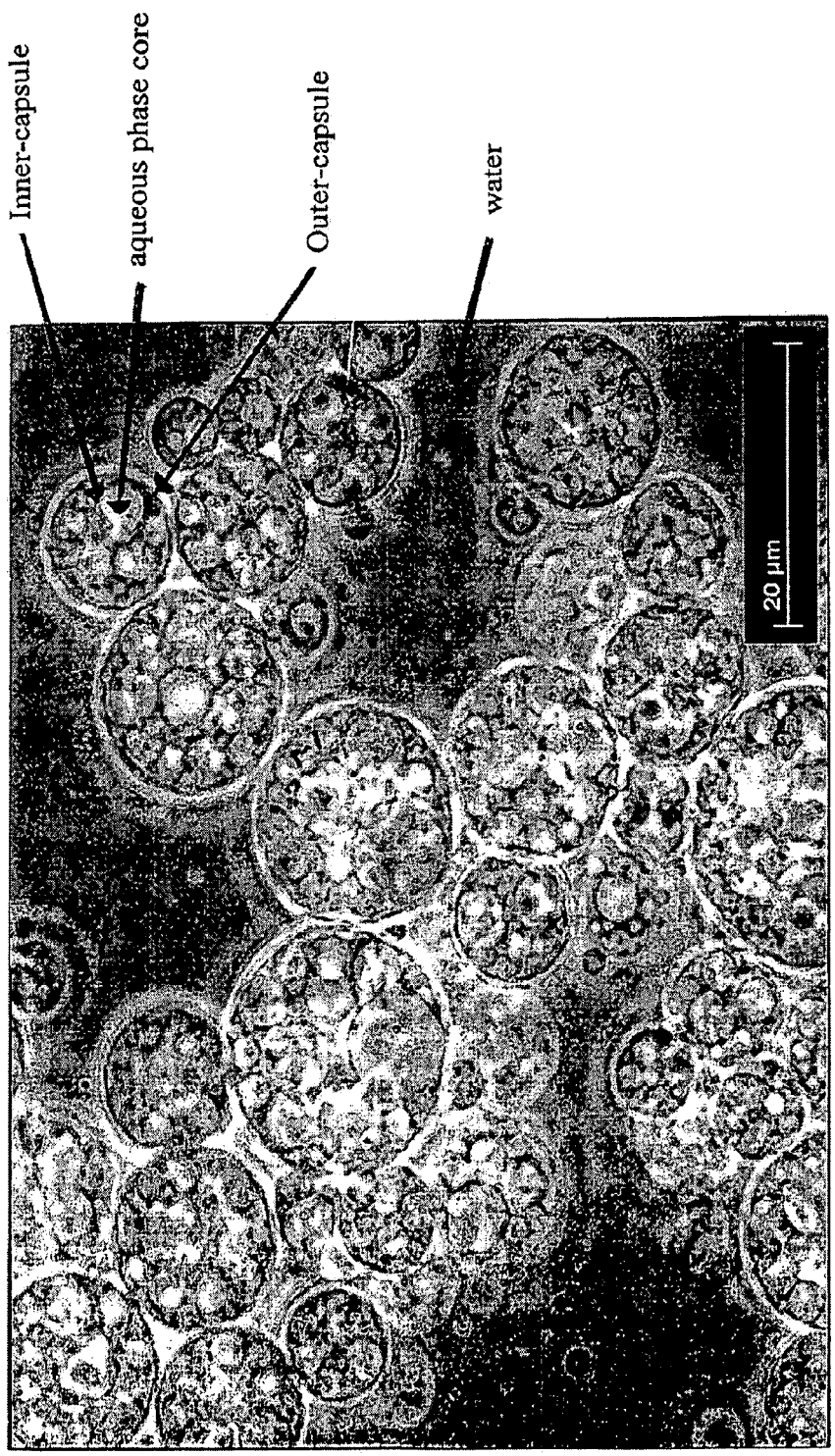
FIG. 2 is a micrograph showing representative polynuclear microcapsules of the invention.

Alkyl means a linear or branched hydrocarbon radical. The number of carbon atoms is expressed for example as "$C_1$-$C_5$", indicating that the alkyl radical has from 1 to 5 carbon atoms.

Alkylene means an organic radical formed from an unsaturated aliphatic hydrocarbon; for example ethylene.

Entrapped means that the hydrophilic active that is encapsulated in the polynuclear microcapsule can not freely diffuse in or out of the polynuclear microcapsule.

Organofunctional silica is the reaction product obtained from the polymerization of a mixture of one or more tetraalkoxysilane and one or more trialkoxysilane, dialkoxysilane or monoalkoxysilane or the reaction product obtained from polymerization of a mixture of any combination of trialkoxysilanes, dialkoxysilanes or monoalkoxysilanes.

Volume particle size equals the diameter of a sphere that has same volume as a given particle.

The terms "hydrophilic materials" and "hydrophilic actives" are used interchangeably.

Stabilization means to prevent or slow deactivation of a biologic. For example an encapsulated biologic is stabilized when the activity of the biologic is maintained for a longer period of time than if unencapsulated.

ABBREVIATIONS

TMOS tetramethoxysilane
TEOS tetraethoxysilane
ml milliliters
µm micrometer
g grams
mM millimolar One embodiment of the invention is a process for preparing polynuclear microcapsules. Step I of the process of the present invention to prepare polynuclear microcapsules comprises mixing;
  A) a first emulsifier,
  B) an alkoxysilane,
  C) a hydrophilic active
with water to form an emulsion having the alkoxysilane in the continuous phase.

Step II of the process comprises admixing to the emulsion having the alkoxysilane in the continuous phase
  D) a second emulsifier
to form a multiple phase emulsion having multiple oil/water interfaces.

Step III comprises polymerizing the alkoxysilane at the oil/water interfaces of the multiple phase emulsion to form the suspension of polynuclear microcapsules.

A) The First Emulsifier

Component A) may be any molecule or particle capable of orientating at the interface between an aqueous or hydrophilic phase and a hydrophobic phase, wherein the resulting emulsion has the hydrophobic phase as the continuous phase (for example a water in oil or inverse emulsion). The aqueous or hydrophilic phase may also contain a hydrophilic cosmetic, chemical, biological or pharmaceutical active material. Suitable first emulsifiers may be selected from surfactant molecules considered to be water/oil or water/silicone emulsifiers, such as nonionic surfactants having an HLB≦8. Some representative examples include, but are not limited to, silicone polyethers, aminofunctional silicones, sorbitan derivatives, alkoxylated alcohols, alkoxylated amides, trans-esters, lanoline derivatives, amino acid derivatives, alkoxylated carboxylic acids derivatives, alkoxylated amines, polymeric ethers derivatives, glyceryl esters and derivatives, polysaccharides derivatives. Such emulsifiers include particles treated or not, including but not limited to, treated silica, such as fumed or colloidal silica, treated clays, or synthetic clays such as laponite.

Component A) may be selected from any emulsifier that is typically classified as a water/oil or a water/silicone emulsifier.

In one embodiment of the present invention, the organopolysiloxane having at least one hydrophilic substituent group is selected from silicone polyethers. Silicone polyethers (SPEs) generally refer to silicones containing polyether or polyoxyalkylene groups, which could take in many different structural forms. Typically such forms are either rake-type or ABA type SPEs which are derived most commonly from hydrosilylation of SiH functional organosiloxanes with allyloxy-functional polyethers in the presence of a Pt catalyst. In this embodiment, component (A) is a silicone polyether having the structure represented by:

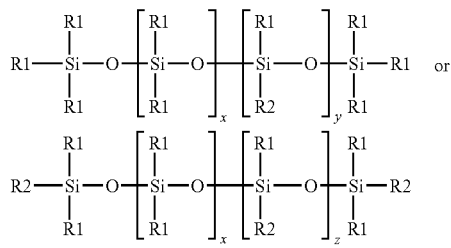

In these structures, R1 represents a $(C_1-C_6)$ alkyl group for example: methyl, ethyl, propyl, butyl, pentyl, and hexyl; R2 represents the group $-(CH_2)_aO(C_2H_4O)_b(C_3H_6O)_cR3$;

x has a value of 1-1,000, alternatively 1-500, or alternatively 100-500;

y has a value of 1-500, alternatively 1-100, or alternatively 1-20;

z has a value of 1-500, or alternatively 1-100;

a has a value of 3-6;

b has a value of 1-40;

c has a value of 0-40; and

R3 is hydrogen, a methyl group, or an acyl group such as acetyl.

The silicone polyethers disclosed in U.S. Pat. No. 4,122,029 may be selected as component A) and is herein incorporated by reference in its entirety for its teaching of polydiorganosiloxanepolyoxyalkylene block copolymers containing at least one polydiorganosiloxane block and at least one polyoxyalkylene block.

An illustrative, non-limiting silicone polyether useful as component A) is

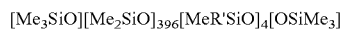

[Me$_3$SiO][Me$_2$SiO]$_{396}$[MeR'SiO]$_4$[OSiMe$_3$]

where Me is $-CH_3$ and R' is $-(CH_2)_3(EO)_{18}(PO)_{18}OH$ containing 3-40 carbon atoms.

The silicone polyethers disclosed in U.S. Pat. No. 4,853,474 may be selected as component A) and is herein incorporated by reference in its entirety for its teaching of organopolysiloxane-polyoxyalkylene emulsifiers for polar in nonpolar liquid emulsions wherein the organopolysiloxane-polyoxyalkylene polymer molecules are intentionally cross linked through a cross linking agent joined thereto by non-hydrolyzable bonds and being free of internal hydrolyzable bonds.

Silicone polyether elastomers such as those disclosed in U.S. Pat. No. 5,811,487 may be selected as component A) and is herein incorporated by reference in its entirety for its teaching of elastomeric silicone polyethers useful as component A).

In another embodiment, component A) may be selected from an amino functional organopolysiloxane, such as those represented by the following formula;

[Me$_3$SiO][Me$_2$SiO]$_{1-1000}$[MeR$^3$SiO]$_{1-100}$[OSiMe$_3$]

where Me is $-CH_3$ and R$^3$ is an amine functional organic group such as $-(CH_2)_3NH_2$, $-(CH_2)_3NH(CH_2)_2NH_2$ or, $-CH_2CH(CH_3)CH_2NH(CH_2)_2NH_2$ The first emulsifier may also be a combination or mixture of various emulsifiers, for example any of those described above. The first emulsifier may also include the addition of auxiliary surfactants. Furthermore, the emulsifier or mixture of emulsifiers may be used neat, or the emulsifier may be dissolved in a hydrophobic solvent, such as a volatile silicone.

Commercial products suitable as component A) include, but are not limited to: DC5225C, DC3225C, DC5200, DC9011, DC9040, DC9050 DC8822A, (Dow Corning Corp., Midland, Mich. 48686). The first emulsifier may also be an organic based W/O emulsifier like sorbitan isostearate, sorbitan stearate, polyglyceryl oleate, lecithin, sorbitan monooleate, sorbitan trioleate, sorbitan laurate, glyceryl monooleate, lanolin and lanolin alcohols, PEG-30 Dipolyhydroxystearate, steareth-2, hydrogenated palm glycerides, polyglyceryl-3-diisostearate, polyglyceryl-4-diisostearate, polyglyceryl-3-polyricinoleate, sorbitan sesquioleate, PEG-2 Hydrogenated castor oil, PEG-7 Hydrogenated castor oil, polyperfluoroethoxymethoxy difluoromethyl distearamide, cholesterol or a combination thereof and not limited to this list.

B) The Alkoxysilane

Component B) is an alkoxysilane. As used herein the term "alkoxysilane" means a compound or a mixture of compounds, wherein each compound is independently selected from compounds having the formula $R_nSi(OR^5)_{(4-n)}$ where n=0-3 and R represents an organic group, and $R^5$ is a hydrocarbon group having 1 to 8 carbons or hydrogen. Examples of alkoxysilanes include, but are not limited to, tetraethoxysilane, tetramethoxysilane, methyltrimethoxysilane, diethyldiethoxysilane, dimethyldimethoxysilane and trimethylmonomethoxysilane.

C) The Hydrophilic Active

Optional component C) is a hydrophilic active.

The hydrophilic active may be solvated in water or a water soluble solvent. Water soluble solvents include, but are not limited to alcohols, such as ethanol.

Some representative examples of hydrophilic actives include; drugs, vitamins, antioxidants, hormones, topical antimicrobial agents such as antibiotics, antifungals for example those used for the treatment of athlete's foot, jock itch, or ringworm, and acne; astringents; deodorants; wart removers; corn and callus removers; pediculicides for example, those used for the treatment of head, pubic (crab), and body lice; agents for the control of dandruff, seborrheic dermatitis, or psoriasis; colorants for example FD&C blue No. 1, FD&C blue No. 2, FD&C green No. 3, FD&C red No. 40, FD&C yellow No. 5, FD&C yellow No. 6; metaloxides, for example: titanium dioxide or iron oxides; and sunburn prevention and treatment agents.

Vitamins useful herein include, but are not limited to, Vitamin A$_1$, retinol, C$_2$-C$_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin B$_1$, Vitamin B$_2$, Pro Vitamin B5, panthenol, Vitamin B$_6$, Vitamin B$_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

Some examples of commercially available products suitable for use herein are Vitamin A Acetate product of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active component C) of the present invention can be a biologic, such as an enzyme or cell. Encapsulation of biologics, for example enzymes, in the polynuclear microcapsules of the invention may prevent or slow deactivation of the enzyme or biologic thus maintaining activity for a longer period of time than if unencapsulated.

Enzymes include, but are not limited to, commercially available types, improved types, recombinant types, wild types, variants not found in nature, and mixtures thereof. For example, suitable enzymes include, but are not limited to, hydrolases, cutinases, oxidases, transferases, reductases, hemicellulases, esterases, isomerases, deamidases, decarboxylases, lyases, peptidases, racemases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Peptidases include, but are not limited to, thermolysin and trans-glutaminase.

Proteases include, but are not limited to, trypsin, chymotrypsin, pepsin, pancreatin and other mammalian enzymes; papain, bromelain and other botanical enzymes; subtilisin, epidermin, nisin, naringinase (L-rhammnosidase), urokinase and other bacterial enzymes.

Lipases include, but are not limited to, triacyl-glycerol lipases, monoacyl-glycerol lipases, lipoprotein lipases, e.g. steapsin, erepsin, pepsin, other mammalian, botanical, bacterial lipases and purified ones. Further, stimulating hormones, e.g. insulin, can be used together with these enzymes to boost the effectiveness of them.

Biologics can be isolated from a variety of natural sources and may be produced by biotechnology methods. Biologics may comprise sugars, proteins, or nucleic acids, or complex combinations of the same. Biologics also may be living entities. Examples of such living entities include, but are not limited to, mammalian cells and microorganisms such as fungi, bacteria and yeasts. Biologics also include mammalian tissues; cell bodies such as cell nuclei, mitochondria and ribosomes.

The biologics described herein include both medicinal and non-medicinal biologics. Specific examples of medicinal biologics include, but are not limited to, vaccines, blood and blood components, allergenics, and therapeutic biologics. Specific examples of biologics useful as therapeutic biologics include monoclonal antibodies or fragments thereof, recombinant proteins, RNAi, aptamers, and dendrimers, RNA, and DNA.

Non-medicinal biologics include biologics used in industrial processes or products. For example: detergent enzymes for use in laundry detergents; enzymes for the starch, textile and bioethanol industries; food enzymes for dairy, baking, brewing, and wine industries; and feed enzymes for the animal feed industries. Other non-medicinal biologics include microorganisms for use in cleaning, wastewater treatment, aquaculture and plant care. Biologics also include proteins that may be used to catalyse chemical reactions, for example: specially designed enzymes may be used to catalyze industrially relevant chemical reaction such in the synthesis of organic molecules such as drugs.

Components A), B), and C) are mixed with water or a water soluble solvent to form an emulsion having the alkoxysilane in the continuous phase. The amounts of components A), B), C), and water/water soluble solvent may vary, but typically range as follows as based on weight percents of each component;
A) 0.1 to 30, or 0.5 to 20, or 1 to 10,
B) 1 to 99, or 10 to 90, or 15 to 50,
C) 0.01 to 90, or 1 to 99, or 10 to 90, or 50 to 85,
and sufficient water or water soluble solvent to total to 100 weight percent.

Mixing and emulsion formation of step II in present process may occur using any known techniques in the art, and in particular, those useful for the formation of water in oil, oil continuous, or inverse emulsions. Typically, the hydrophobic phase (components A and B) and hydrophilic phase (component C and water or water soluble solvent) are combined using simple stirring techniques to form an emulsion having the component B (the alkoxysilane) in the continuous phase. If simple stirring techniques are used, at this stage the emulsion has a particle size typically classified as a "coarse" emulsion. Particle size of the emulsion may then be reduced by further shearing using any known in the art emulsification device to produce a "fine" emulsion. Useful emulsification devices in this invention can be static mixer, homogenizer, sonolator, Ultra Sonic probes, rotor-stator turbines, colloid mill, microfluidizer, blades, helix and combination thereof but is not limited to this list of emulsification devices. This further processing step reduces the particle size of the starting water in oil emulsion to values ranging from 0.2 to 500 micrometers, with typical particle sizes ranging between 0.5 micrometers and 100 micrometers.

The weight ratio of the hydrophilic phase to the continuous hydrophobic phase in the emulsion is generally between 40:1 and 1:50. Usually the weight ratio of hydrophilic phase to hydrophobic continuous phase is between 4:1 and 1:4.

D) The Second Emulsifier

Step II in the process of the present invention involves adding a second emulsifier to the emulsion having the alkoxysilane in the continuous phase to form a multiple phase emulsion. The second emulsifier may be selected from any emulsifier known in the art to stabilize oil in water or water continuous emulsions. The second emulsifier can be used either alone or in combination with other emulsifiers. Typically, the second emulsifier is selected from a cationic, nonionic, anionic, or zwitterionic surfactant. Typically, an aqueous solution of the second emulsifier is used in step II.

Cationic surfactants useful as the second emulsifier in this invention are quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, for example, cetyl trimethyl ammonium chloride; fatty amines and fatty acid amides and their derivatives, basic pyridinium compounds, quaternary ammonium bases of benzimidazolines and polypropanolpolyethanol amines but is not limited to this list of cationic surfactants. The cationic surfactant may also be a polymer or copolymer such as Eudragit® E 100 (Acrylates/Dimethylaminoethyl Methacrylate Copolymer).

The second emulsifier may also be selected from an amphoteric surfactant such as cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds but is not limited to this list of amphoteric surfactants.

The above surfactants may be used individually or in combination. The cationic or amphoteric surfactant is dissolved in water and the resulting aqueous solution used as a component in aqueous or continuous phase of the oil in water emulsion of step I.

Suitable non-ionic surfactants are: polyoxyalkylene alkyl ethers such as, polyethylene glycol long chain ($C_{12}$-$C_{14}$) alkyl ether; polyoxyalkylene sorbitan ethers; polyoxyalkylene alkoxylate esters; polyoxyalkylene alkylphenol ethers; ethylene glycol propylene glycol copolymers, such as block copolymers of the formula $(EO)_{1-200}(PO)_{1-200}(EO)_{1-200}$; polyvinyl alcohol; and alkylpolysaccharides, for example materials of the structure $R^1$—O—$(R^2O)_m$-$(G)_n$ wherein $R^1$ represents a linear or branched ($C_8$-$C_{50}$) alkyl group, a linear or branched ($C_8$-$C_{50}$) alkenyl group or a ($C_8$-$C_{50}$) alkylphenyl group, $R^2$ represent a ($C_8$-$C_{50}$) alkylene group, G represents a reduced sugar, m denotes 0 or a positive integer and n represent a positive integer as described in U.S. Pat. No. 5,035,832 but is not limited to this list of non-ionic surfactants. Other suitable emulsifiers include particles treated or not, including but not limited to, treated silica, such as fumed or colloidal silica, treated clays, or synthetic clays such as laponite.

Component D may also be an acrylate copolymer known in the art to stabilize emulsions, such as Pemulen® TR1 and Pemulen® TR2 (Acrylates/C10-30 Alkyl Acrylate Crosspolymer).

Component D may also be a mixture of emulsifiers including the addition of auxiliary surfactants. When used, the auxiliary surfactants may be selected from non-ionic surfactants, such as an ethoxylated fatty alcohol like Laureth-3.

The amount of component D added to the emulsion from step I may vary but typically ranges from 0.1 to 20 wt % of the emulsion, or 0.25 to 10 wt % of the emulsion, or 0.5 to 5 wt % of the emulsion.

Component D is added to the emulsion from step I and sufficiently mixed to form a multiple phase emulsion. Typically, the emulsion from step I is added to an aqueous solution of component D with mixing. The mixing technique is not critical, and may be any mixing method, especially those known in the art for effecting the formation of oil/water emulsions. Useful devices to effect this mixing include static mixers, homogenizers, sonolators, ultra Sonic probes, rotor-stator turbines, colloid mills, microfluidizers, blades, helix and combinations thereof, but is not limited to this list of emulsification devices.

A multiple phase emulsion forms as a result of the process of Step II. Multiple phase emulsions are sometimes referred to as "triple emulsions". The formation of the multiple phase emulsion in Step II may be confirmed by known microscopic observations of the particles.

Step III in the process of the present invention involves polymerizing the alkoxysilane at the oil/water interface of the multiple phase emulsion to form a suspension of polynuclear microcapsules.

The polymerization of the alkoxysilane at the oil/water interface typically is a condensation reaction which may be conducted at acidic, neutral or basic pH. The condensation reaction is generally carried out at ambient temperature and pressure, but can be carried out at increased temperature, for example up to 95° C., and increased or decreased pressure, for example under vacuum to strip the volatile alcohol produced during the condensation reaction. The condensation reaction may be monitored by the non-volatile content of the reaction mixture. The alkoxysilane will generate a volatile alcohol during the condensation reaction. Thus, volatile content will provide a stoichiometric correlation with the reaction progress. The non-volatile content may be monitored by any means known, e.g. heating the reaction samples until the samples reach a constant mass.

Any catalyst known to promote the polymerization of the alkoxysilane may be added to step III to form the shell of the polynuclear microcapsule. The catalyst is preferably an oil soluble organic metal compound, for example an organic tin compound, particularly an organotin compound such as a diorganotin diester, for example dimethyl tin di(neodecanoate), dibutyl tin dilaurate or dibutyl tin diacetate, or alternatively a tin carboxylate such as stannous octoate, or an organic titanium compound such as tetrabutyl titanate. An organotin catalyst can for example be used at 0.05 to 2% by weight based on the water reactive silicon compound. An organotin catalyst has the advantage of effective catalysis at neutral pH. The catalyst is typically mixed with the oil phase components before it is emulsified, since this promotes condensation of the water reactive silicon compound at the surface of the emulsified oil phase droplets. A catalyst can alternatively be added to the emulsion before the addition of the water-reactive silicon compound, or simultaneously with the tetraalkoxysilane, or after the addition of the tetraalkoxysilane to harden and make more impervious the shell of silicon-based polymer which has been formed. Encapsulation can however be achieved without catalyst. The catalyst, when used, can be added undiluted, or as a solution in an organic solvent such as a hydrocarbon, alcohol or ketone, or as a multiphase system such as an emulsion or suspension.

The formed polynuclear microcapsules from step III typically remain in suspension. The aqueous continuous phase may contain water miscible organic solvent; for example it usually contains an alcohol such as ethanol generated by hydrolysis of Si-bonded alkoxy groups. It may be advantageous to use the suspension of microcapsules in a water based preparation, for example a cosmetic, chemical or pharmaceutical product without separating the polynuclear microcapsules from the suspension.

For many uses the polynuclear microcapsules are recovered from suspension, for example for subsequent dispersion in a different medium. An encapsulated active in the polynuclear microcapsule may be dispersed in a water based cosmetic preparation. Alternatively the polynuclear microcapsules can be re-dispersed in an organic solvent, optionally with additives such as surfactant and/or polymer.

Recovery of the polynuclear microcapsules can be achieved by any known liquid removal technique, for example by spray drying, spray chilling, filtering, oven drying or lyophilisation.

The present invention thus further relates to the microcapsule suspension, and isolated microcapsules, as prepared according to the processes as described above.

The polynuclear microcapsules of the invention may be used for example, for the entrapment of hydrophilic actives or for controlled or triggered delivery systems for the hydrophilic active. Hydrophilic actives suitable for entrapment in the polynuclear microcapsules of the invention include those described above in the section relating to the processes of the invention. In an embodiment of the invention the polynuclear microcapsule comprises a vitamin or antioxidant. In another embodiment the polynuclear microcapsule comprises a sun screen agent. In an embodiment the polynuclear microcapsule provides entrapment of a larger hydrophilic active such as a protein but allows smaller molecules to freely diffuse in and out of the polynuclear microcapsule. In another embodiment of the invention the polynuclear microcapsule comprises a biologic. In one embodiment the polynuclear microcapsule comprises a therapeutic biologic. In another embodiment the polynuclear microcapsule comprises a cell.

In another embodiment the polynuclear microcapsule comprises a microorganism. In another embodiment the microcapsule comprises a protein. For example, the polynuclear microcapsule may comprise an enzyme such as catalase and allow for its substrate, $H_2O_2$, to freely diffuse in and out of the polynuclear microcapsule. Thus in another the polynuclear microcapsules comprise an enzyme. In another embodiment the polynuclear microcapsules are used to stabilize the hydrophilic active. In another embodiment the polynuclear microcapsules are used to facilitate the separation of the entrapped hydrophilic active from a molecule that is not entrapped. In another embodiment the polynuclear microcapsules are used to increase the shelf-life of a pharmaceutical ingredient. In another embodiment of the invention the polynuclear microcapsules are used for industrial processes or products. In another embodiment the polynuclear microcapsules are used to catalyse chemical reactions such as in the synthesis of organic molecules such as drugs. In another embodiment of the invention the polynuclear microcapsules are used in cleaning, wastewater treatment, aquaculture and plant care. In another embodiment the polynuclear microcapsules comprise detergent enzymes, food enzymes, or feed enzymes.

The polynuclear microcapsule of the invention comprises a plurality of inner-capsules. In one embodiment the polynuclear microcapsule comprises between 2 and 10,000 inner-capsules. In another embodiment the polynuclear microcapsule comprises between 2 and 1000 inner-capsules. In another embodiment the polynuclear microcapsule comprises between 50 and 500 inner-capsules. In another embodiment the polynuclear microcapsule comprises between 100 and 500 inner-capsules.

One of skill in the art would recognize that depending on the use, it may be desirable to use polynuclear microcapsule having different porosities. For example if encapsulation of the hydrophilic active is desired for example, to prevent direct contact with a surface, e.g. skin or fabric, it may be desirable to have low porosity. In this case, a lower ratio of water to oil may be used to obtain the porosity desired.

In contrast, where the hydrophilic active is encapsulated but the use requires that low molecular weight molecules be able to diffuse in and out of the polynuclear microcapsule, it may be desirable to have a higher degree of porosity. In this case, a higher water to oil ratio may be used to obtain the porosity desired.

One of skill in the art would also recognize that the porosity of the polynuclear microcapsule can also be controlled by using tri, di and monoakoxysilanes in addition to or instead of tetralkoxysilanes.

The porosity may be controlled by any of the above method, alone or in combination. The above examples are illustrative and are not intended to be limiting.

The average volume particle size of a polynuclear microcapsule of the invention is between 0.05 µm and 1000 µm; or between 0.5 µm and 1000 µm; or between 1 µm and 500 µm; or between 5 and 100 µm; or between 10 µm and 50 µm; or between 0.5 µm and 20 µm; or between 0.05 µm and 20 µm.

The particle size of microcapsules is measured by laser diffraction of a suspension of microcapsules. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the polynuclear microcapsules. Dv 0.5 is the particle size measured in volume corresponding to 50% of the cumulative particle population. In other words if Dv 0.5=10 µm, 50% of the particle have an average volume particle size below 10 µm and 50% of the particle have a volume average particle size above 10 µm. Unless indicated otherwise all average volume particle sizes are calculated using Dv 0.5.

EXAMPLES

The following examples are intended to illustrate the invention to one of ordinary skill in the art and should not be interpreted as limiting the scope of the invention set forth in the claims.

The process of the present invention was used in the following examples to prepare the polynuclear microcapsules of the invention. These examples demonstrate that a hydrophilic active, for example an enzyme, may be entrapped and that the activity of the entrapped hydrophilic active, for example the activity of an enzyme, is stabilized when it is encapsulated in the polynuclear microcapsules of the invention.

The results of the experiments of Examples 1-18 show that, under a variety of conditions, that the activity of the encapsulated catylase enzyme was maintained for a longer period of time than was the activity of the unencapsulated enzyme.

All measurements and experiments were conducted at 23° C., unless indicated otherwise. Because it is well known in the art that hydrolysis and condensation of alkoxysilanes are greatly dependent of pH, the encapsulation was conducted at three different pH in order to measure pH impact on, for example, enzyme diffusion, activity and stabilization.

Example 1

First, 5 g of Dow Corning® 5225c Formulation aid (Dow Corning Corporation, Midland Mich.) was mixed with 25 g of tetraethoxysilane (TEOS). Then, 70 g of water at pH 4.5 were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, 20 g of the fine inverse emulsion was mixed for 20 seconds with 20 g of an aqueous solution (pH=4.5) of 1 wt. % cetyltrimethylammonium chloride (CTAC) and 1.25 wt. % of a Laureth 3 surfactant using a Hauschild type AM 501 mixer, which resulted in the formation of a water continuous emulsion. The TEOS in the mixture was allowed to completely hydrolyze and condense for 10 hours at pH 4.5 resulting in the formation of a suspension of polynuclear microcapsules having an average volume particle size (Dv 0.5) of 18.6 micrometers.

Example 2

First, 5 g of Dow Corning® 5225c Formulation aid (Dow Corning Corporation, Midland Mich.) was mixed with 25 g of tetraethoxysilane (TEOS). Then, 70 g of water at pH 4.5 containing 0.07 g of NaCl were added and mixed to form a coarse emulsion having TEOS in the continuous phase, i.e. an inverse emulsion. The coarse inverse emulsion was then further sheared with a rotor/stator type mixer (IKA® Ultra-Turrax Basic 25) at 9500 rpm for one minute to reduce particle size and form a fine inverse emulsion. Then, 20 g of the fine inverse emulsion was mixed for 20 seconds with 20 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The TEOS in the resulting emulsion was allowed to completely hydrolyze and condense for 10 hours at pH 4.5 resulting in the formation of a suspension of polynuclear microcapsules having an average volume particle size (Dv 0.5) of 11.6 micrometers.

Example 3

First, 5 g of Dow Corning® 5225c Formulation aid (Dow Corning Corporation, Midland Mich.) was mixed with 25 g of tetraethoxysilane (TEOS). Then, 70 g of water at pH 4.5 containing 0.35 g Vitamin C were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, 20 g of the fine inverse emulsion was mixed for 20 seconds with 20 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The TEOS in the resulting emulsion was allowed to completely hydrolyze and condense for 10 hours at pH 4.5 resulting in the formation of a suspension of polynuclear microcapsules having an average volume particle size (Dv 0.5) of 20.4 micrometers.

Example 4

First, 5 g of Dow Corning® 5225c Formulation aid (Dow Corning Corporation, Midland Mich.) was mixed with 25 g of tetraethoxysilane (TEOS). Then, 70 g of water at pH 4.5 containing 0.35 g Catalase enzyme were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, 20 g of the fine inverse emulsion was mixed for 20 seconds with 20 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The TEOS in the resulting emulsion was allowed to completely hydrolyze and condense for 10 hours at pH 4.5 resulting in the formation of a suspension of polynuclear microcapsules having an average volume particle size (Dv 0.5) of 18 micrometers.

Example 5

First, 5 g of Dow Corning® 5225c Formulation aid (Dow Corning Corporation, Midland Mich.) was mixed with 25 g of tetraethoxysilane (TEOS). Then, 70 g of water at pH 4.5 containing 0.35 g Bovine Serum Albumin (BSA) protein were added and mixed to form a coarse emulsion having TEOS in the continuous phase, i.e. an inverse emulsion. The coarse inverse emulsion was then further sheared with a rotor/stator type mixer (IKA® Ultra-Turrax Basic 25) at 9500 rpm for one minute to reduce particle size and form a fine inverse emulsion. Then, 20 g of the fine inverse emulsion was mixed for 20 seconds with 20 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The TEOS in the resulting emulsion was allowed to completely hydrolyze and condense for 10 hours at pH 4.5 resulting in the formation of a suspension of polynuclear microcapsules having an average volume particle size (Dv 0.5) of 27.5 micrometers.

Example 6

First, 5 g of Dow Corning® 5225c Formulation aid (Dow Corning Corporation, Midland Mich.) was mixed with 25 g of tetraethoxysilane (TEOS). Then, 70 g of water at pH 4.5 were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. The polymerization reaction was monitored by measurement of the silica produced during the hydrolysis and condensation of the TEOS. The non volatile content may be monitored by any means known. In these examples, reaction samples were placed in a thermal oven and allowed to reach a constant mass. After 40% of the TEOS hydrolysed and condensed to silica, 20 g of the emulsion was mixed for 20 seconds with 20 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The remaining TEOS in the mixture was allowed to completely hydrolyze and condense for 10 hours at pH 4.5 resulting in the formation of a suspension of polynuclear microcapsules having an average volume particle size (Dv 0.5) of 14.2 micrometers.

Example 7

First, 5 g of Dow Corning® 5225c Formulation aid (Dow Corning Corporation, Midland Mich.) was mixed with 25 g of tetraethoxysilane (TEOS). Then, 70 g of water at pH 4.5 were added and mixed to form a coarse emulsion having TEOS in the continuous phase, i.e. an inverse emulsion. The coarse inverse emulsion was then further sheared with a rotor/stator type mixer (IKA® Ultra-Turrax Basic 25) at 9500 rpm for one minute to reduce particle size and form a fine inverse emulsion. The polymerization reaction was monitored as in example 6. After 80% of the TEOS hydrolysed and condensed to silica, 20 g of the emulsion was mixed for 20 seconds with 25 g of an aqueous solution (pH=4.5) of 1 wt. % cetyltrimethylammonium chloride (CTAC) and 1.25 wt. % of Laureth 3 using a Hauschild type AM 501 mixer, which resulted in the formation of a water continuous emulsion. The remaining TEOS in the mixture was allowed to completely hydrolyze and condense for 5 hours at pH 4.5 resulting in the formation of a suspension of polynuclear microcapsules having an average volume particle size (Dv 0.5) of 33.3 micrometers.

Example 8

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.2 g Catalase enzyme were added and mixed to form a coarse emulsion having TEOS in the continuous phase (i.e. an inverse emulsion). The catalase was purchased from Sigma-Aldrich Corp, St. Louis Mo. as a lyophilized powder having 2,000-5000 units/mg. One unit is the amount of enzyme that will decompose 1.0 µmole of $H_2O_2$ per min at pH 7 at 25° C., while the $H_2O_2$ conc. falls from 10.3 to 9.2 mM, measured by the rate of decrease of $A_{240}$. The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=7) of 1.25 g PLURONIC® F127 (an ethylene glycol propylene glycol block copolymer having the formula $(EO)_{98}(PO)_{67}(EO)_{98}$ sold by BASF Corp, 3000 Continental Drive-North, Mount Olive, N.J. 07828-1234) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 17.6 micrometers.

The catalase enzyme present in the external water phase of the suspension was assayed by the Biuret protein assay method which is well known in the art. Briefly, samples of unknown catalase concentration are obtained after separation of the polynuclear microcapsule from the continuous phase. Standard samples are prepared using bovine serum albumin (Merck) at 0.5, 1, 2, 3, 4 and 5 grams per liter. One ml of sample or standard solution is added to 2 ml of Bioquant® reagent, Merck KGaA, Darmstadt. The samples are mixed and incubated for 30 minutes at room temperature. The samples are put into a 1 centimeter plastic cuvette and the absorbance at 546 nm is measured against a blank of double distilled water. The amount of catalase in a sample is determined by comparison of a standard curve generated from the measurements of the standard solution.

As determined by the Biuret assay, no catalase was detected in the external water phase demonstrating that all the catalase was entrapped inside the polynuclear microcapsules. Using the Biuret assay, the diffusion of catalase was monitored over time. No diffusion was observed over a 49 day period.

Example 9

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.2 g of Bovine Serum Albumin (BSA) were added and mixed to form a coarse emulsion having TEOS in the continuous phase, i.e. an inverse emulsion. The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=7) of 1.25 g PLURONIC® F127 (BASF Corp, 3000 Continental Drive-North, Mount Olive, N.J. 07828-1234) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 22.5 micrometers.

Bovine Serum Albumin (BSA) present in the external water phase of the suspension was assayed by the Biuret assay, as described in example 8. No BSA was detected in the external water phase demonstrating that all the BSA was entrapped inside the polynuclear microcapsules. Using the Biuret assay, the diffusion of catalase was monitored over time. No diffusion was observed over a 49 day period.

Example 10

First, 3 g of Dow Corning® 8822A Polymer (Dow Corning Corporation, Midland Mich.) was mixed with 20 g of tetraethoxysilane (TEOS). Then, 50 g of water at pH 4 containing 0.2 g Catalase enzyme were added and mixed to form a coarse emulsion having TEOS in the continuous phase, i.e. an inverse emulsion. The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=7) of 1.25 g PLURONIC® F127 (no CTAC) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 28.6 micrometers.

The catalase enzyme present in the external water phase of the suspension was assayed by the Biuret assay as described in example 8. No catalase was detected in the external water phase demonstrating that all the catalase was entrapped inside the polynuclear microcapsules. Using the Biuret protein assay, the diffusion of catalase was monitored over time. No diffusion was observed over a 49 day period.

Example 11

First, 6 g of Dow Corning® 5225c Formulation aid (5225c) was mixed with 20 g of Tetraethoxysilane (TEOS). Then, 50 g of polyethylene glycol (Polyethylene Glycol 400) was mixed in the 5225C/TEOS blend to form a coarse polyethylene glycol in TEOS inverse emulsion. The particle size was reduced by shearing the coarse inverse emulsion with a rotor/stator IKA® Ultra-Turrax Basic 25 type mixer at 9500 rpm for 60 seconds to produce a fine emulsion. Then, the fine emulsion was inverted by the addition of 100 g of a pH 4 water solution containing 1.25 g PLURONIC® F127 and mixed with a Hauschild type AM 501 mixer for 20 seconds. After complete hydrolysis and condensation of TEOS, Polyethylene Glycol 400 in silica polynuclear microcapsules of average volume particle size (Dv 0.5) 28.7 micrometers were produced in water suspension.

Example 12

First, 6 g of Dow Corning® 5225c Formulation aid (5225c) was mixed with 20 g of Tetraethoxysilane (TEOS). The, 50 g of propylene glycol was mixed in the 5225C/TEOS blend to form a coarse propylene glycol in TEOS inverse emulsion. The particle size was reduced by shearing the coarse inverse emulsion with a rotor/stator IKA® Ultra-Turrax Basic 25 type mixer at 9500 rpm for 60 seconds to produce a fine emulsion. Then, the fine emulsion was inverted by the addition of 100 g of a pH 4 water solution containing 1.25 g PLURONIC® F127 and mixed with a Hauschild type AM 501 mixer for 20 seconds. After complete hydrolysis and condensation of TEOS, propylene glycol in silica polynuclear microcapsules of average volume particle size (Dv 0.5) 28.7 micrometers were produced in water suspension.

Example 13

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.0005 g of blue dye (FD&C Blue no 1) were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 30 seconds with 100 g of an aqueous solution (pH=4) containing 1.25 g PLURONIC® F127 using a Hauschild type AM 501 mixer, which resulted in the formation of a water continuous emulsion. The TEOS in the mixture was allowed to completely hydrolyze and condense for 15 hours at pH 4 resulting in the formation of a suspension of polynuclear microcapsules having an average volume particle size (Dv 0.5) of 39.4 micrometers.

Example 14

Catalase was purchased from Sigma-Aldrich as a lyophilized powder having 2,000-5000 units/mg. One unit is the amount of enzyme that will decompose 1.0 μmole of $H_2O_2$ per min at pH 7 at 25° C., while the $H_2O_2$ conc. falls from 10.3 to 9.2 mM, measured by the rate of decrease of $A_{240}$. A catalase solution was prepared by mixing 50 grams of water at pH 4.5, with 0.2 grams of Catalase enzyme.

The enzymatic activity of the catalase in the catalase solution was measured after 1, 7, 28, 35, 48 and 267 days of storage. Catalase is an oxydo-reductase enzyme. It catalyses the decomposition of hydrogen peroxide to water. Catalase activity is monitored by measuring the decomposition of hydrogen peroxide ($H_2O_2$) using the following procedure.

Nitrogen is bubbled, with mild stirring, in 100 ml of a 50 mM Phosphate Buffer solution having a pI of 110 mM and a pH of 7 until the dissolve oxygen concentration is less than 10%. Oxygen concentration is measured by an WTW® Oxi 340i oxygen pocket meter (Cole-Parmer Instrument Company), equipped with a CellOx® 325 dissolved oxygen sensor (Cellox L.L.C.). The sensor comprises a gold working cathode and a lead counter anode.

During nitrogen bubbling, $H_2O_2$ is added to yield a concentration of 40 mM and then allowed to oxygenate for 3 minutes. Oxygen concentration is measured for 3 minutes to determine the increase in the percent of dissolved oxygen per minute. Then free or encapsulated catalase enzyme is added to a yield a concentration of 9 ppm. Oxygen concentration after the addition of enzyme is measured until oxygen saturation of the solution. The increase in the percent of dissolved oxygen per minute is the oxygenation rate. Enzyme activity is calculated with the following formula: (oxygenation rate after addition of enzyme)−(oxygenation rate before addition of enzyme).
Catalase activity after storage is shown below.

| | Days | | | | | |
|---|---|---|---|---|---|---|
| | 1 | 7 | 28 | 35 | 48 | 267 |
| Activity % $O_2$/minute | 112 | 110 | 0 | 0 | 0 | 0 |

Example 15

A catalase solution was prepared by mixing 50 grams of water at pH 4.5, with 0.2 grams of Catalase enzyme. Ethanol was added to a concentration of 8% v/v. The enzymatic activity of the catalase was measured after 1, 7, 28, 35, 48 and 267 days. Catalase activity was monitored using the procedure described in example 14.
Catalase activity after storage is shown below.

| | Days | | | | | |
|---|---|---|---|---|---|---|
| | 1 | 7 | 28 | 35 | 48 | 267 |
| Activity % $O_2$/minute | 134 | 119 | 119 | 105 | 90 | 0 |

Example 16

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.2 g Catalase enzyme were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=4) of 1.25 g PLURONIC® F127 (an ethylene glycol propylene glycol block copolymer having the formula $(EO)_{98}(PO)_{67}(EO)_{98}$ sold by BASF Corp, 3000 Continental Drive-North, Mount Olive, N.J. 07828-1234) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 17.6 micrometers.

The enzymatic activity of the catalase was measured after 1, 7, 28, 35, 48 and 267 days. Catalase activity was monitored using the procedure described in example 14.
Catalase activity after storage is shown below.

| | Days | | | | | |
|---|---|---|---|---|---|---|
| | 1 | 7 | 28 | 35 | 48 | 267 |
| Activity % $O_2$/minute | 18 | 46 | 82 | 82 | 91 | 96 |

The amount of catalase enzyme present in the external water phase of the suspension was assayed. No catalase was detected in the external water phase demonstrating that all the catalase was entrapped inside the polynuclear microcapsules. The diffusion of catalase was monitored over time. No diffusion was observed over a 49 day period.

Example 17

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.2 g Catalase enzyme were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=7) of 1.25 g PLURONIC® F127 (an ethylene glycol propylene glycol block copolymer having the formula $(EO)_{98}(PO)_{67}(EO)_{98}$ sold by BASF Corp, 3000 Continental Drive-North, Mount Olive, N.J. 07828-1234) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 17.6 micrometers.

The enzymatic activity of the catalase was measured after 1, 7, 28, 35, 48 and 267 days. Catalase activity was monitored using the procedure described in example 14.
Catalase activity after storage is shown below.

|  | Days | | | | | |
| --- | --- | --- | --- | --- | --- | --- |
|  | 1 | 7 | 28 | 35 | 48 | 267 |
| Activity % O$_2$/minute | 42 | 80 | 99 | 94 | 87 | 105 |

The amount of catalase enzyme present in the external water phase of the suspension was assayed as described in example 8. No catalase was detected in the external water phase demonstrating that all the catalase was entrapped inside the polynuclear microcapsules. The diffusion of catalase was monitored over time. No diffusion was observed over a 49 day period.

Example 18

First, 6 g of Dow Corning® 5225c Formulation aid (Dow Corning Corporation, Midland Mich.) was mixed with 20 g of tetraethoxysilane (TEOS). Then, 50 g of water at pH 4.5 containing 0.2 g Catalase enzyme were added and mixed to form a coarse emulsion having TEOS in the continuous phase (i.e. an inverse emulsion). The coarse inverse emulsion was then further sheared with a rotor/stator type mixer (IKA® Ultra-Turrax Basic 25) at 9500 rpm for one minute to reduce particle size and form a fine inverse emulsion. Then, the fine inverse emulsion was mixed for 20 seconds with 100 g of an aqueous solution (pH=8.6) of 1.25 g Pluronic® F127 (an ethylene glycol propylene glycol block copolymer having the formula (EO)98(PO)67(EO)98 sold by BASF Corp, 3000 Continental Drive-North, Mount Olive, N.J. 07828-1234) using a Hauschild type AM 501 mixer, which resulted in the formation of a water continuous emulsion. The TEOS in the resulting emulsion was allowed to completely hydrolyze and condense for 15 hours at pH 7 resulting in the formation of a suspension of polynuclear microcapsules having an average volume particle size (Dv 0.5) of 17.6 micrometers.

The enzymatic activity of the catalase was measured after 1, 7, 28, 35, 48 and 267 days. Catalase activity was monitored using the procedure described in example 14.
Catalase activity after storage is shown below.

|  | Days | | | | | |
| --- | --- | --- | --- | --- | --- | --- |
|  | 1 | 7 | 28 | 35 | 48 | 267 |
| Activity % O$_2$/minute | 50 | 85 | 103 | 112 | 113 | 97 |

The amount of catalase enzyme present in the external water phase of the suspension was assayed as described in example 8. No catalase was detected in the external water phase demonstrating that all the catalase was entrapped inside the polynuclear microcapsules. The diffusion of catalase was monitored over time. No diffusion was observed over a 49 day period.

The invention claimed is:

1. A process for preparing a suspension of polynuclear microcapsules, said polynuclear microcapsules comprising an outer-capsule wherein the outer-capsule comprises an outer-shell and a plurality of inner-capsules, and wherein each of the inner-capsules comprises an inner-shell and an aqueous phase core, and wherein the outer-shell and the inner-shell further comprise a silica or an organofunctional silica, comprising the following steps:
I) mixing
A) a first emulsifier comprising a silicone polyether having the formula I or II:

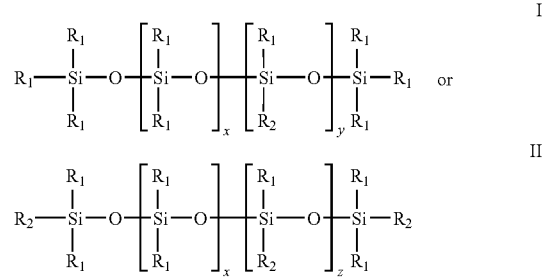

wherein R1 is a (C$_1$-C$_6$)alkyl group,
x is an integer of 1-1000, y is an integer of 1-500, z is an integer of 1-500,
R2 represents the group —(CH$_2$)$_a$O(C$_2$H$_4$O)$_b$(C$_3$H$_6$O)$_c$R3;
a is an integer of 3-6; b is an integer of 1-40; c is an integer of 0-40; and
R3 is hydrogen, a methyl group, or an acyl group
B) an alkoxysilane,
C) a hydrophilic active,
with water to form an emulsion having a continuous phase and a disperse phase wherein the alkoxysilane is in the continuous phase;
II) admixing to the emulsion having the alkoxysilane in the continuous phase
D) a second emulsifier
to form a multiple phase emulsion having multiple oil/water interfaces; and
III) polymerizing the alkoxysilane at the oil/water interfaces of the multiple phase emulsion to form the suspension of polynuclear microcapsules.

2. The process of claim 1 further comprising the step of recovering the polynuclear microcapsules from the suspension.

3. The process of claim 1 wherein the alkoxysilane is tetraalkoxysilane.

4. The process of claim 1 wherein the second emulsifier is a cationic surfactant, a non-ionic surfactant, amphoteric surfactant, or any combination the surfactants.

5. The process of claim 1 wherein the second emulsifier is a polymeric surfactant or particle.

6. The process of claim 5 wherein the polymeric surfactant is an ethylene glycol propylene glycol copolymer.

7. The process of claim 5 wherein the particle is fumed silica, colloidal silica or synthetic clay.

8. The process of claim 1 wherein the weight percent of components A, B and C in step I range from;
A) 0.1 to 30 weight percent, B) 1 to 99 weight percent,
C) 1 to 99 weight percent.

9. The process of claim 8 wherein the weight percent of component D ranges from 0.1 to 20 weight percent in the multiple phase emulsion of step II.

10. The process of claim 1 wherein x is 396, y is 4, a is 3, b is 18, c is 18 and d is 18.

* * * * *